United States Patent [19]
Gordon

[11] Patent Number: 5,634,961
[45] Date of Patent: Jun. 3, 1997

[54] GAS CHROMATOGRAPHY SYSTEM WITH THERMALLY AGILE OVEN

[75] Inventor: Gary B. Gordon, Saratoga, Calif.

[73] Assignee: Hewlett-Packard Company, Palo Alto, Calif.

[21] Appl. No.: 553,215

[22] Filed: Nov. 7, 1995

[51] Int. Cl.$^6$ ................................................. B01D 15/08
[52] U.S. Cl. ........................ 95/17; 95/18; 95/87; 96/102
[58] Field of Search .......................... 73/23.25, 23.26, 73/23.35–23.42; 96/101–107; 422/89; 432/48; 95/14, 17, 18, 82, 87

[56] References Cited

U.S. PATENT DOCUMENTS

| | | | |
|---|---|---|---|
| 3,165,147 | 1/1965 | Roof et al. | 96/102 X |
| 3,305,000 | 2/1967 | Bullen et al. | 96/102 X |
| 3,385,099 | 5/1968 | Diem et al. | 73/23.25 |
| 3,403,545 | 10/1968 | Carter | 73/23.25 |
| 3,422,603 | 1/1969 | Redmond, Jr. | 96/103 |
| 4,050,911 | 9/1977 | Welsh | 96/103 |
| 4,096,908 | 6/1978 | Lamy | 73/23.25 X |
| 4,111,643 | 9/1978 | Welland | 432/36 |
| 4,181,613 | 1/1980 | Welsh et al. | 96/104 X |
| 4,286,456 | 9/1981 | Sisti et al. | 73/23.25 |
| 4,305,276 | 12/1981 | Mueller | 73/23.25 |
| 4,580,036 | 4/1986 | Hunt et al. | 96/101 X |
| 4,599,169 | 7/1986 | Ray | 96/101 X |
| 4,771,628 | 9/1988 | Sisti et al. | 96/101 X |
| 4,869,876 | 9/1989 | Arfman et al. | 96/102 X |

FOREIGN PATENT DOCUMENTS

| | | | |
|---|---|---|---|
| 0086421 | 8/1983 | European Pat. Off. | 422/89 |
| 2921358 | 12/1980 | Germany | 96/102 |
| 60-060556 | 4/1985 | Japan | 73/23.25 |
| 3-291563 | 12/1991 | Japan | 73/23.38 |
| WO82/01662 | 5/1982 | WIPO | 96/101 |

Primary Examiner—Robert Spitzer

[57] ABSTRACT

A high-performance, field-portable, thermally agile, gas chromatography (GC) system employs a low-thermal-mass oven in which intake and exhaust vent apertures are aligned with respect to the rotational axis of the stirring fan. The poppets of the vent dynamically vent to ambient the air-flow generated by the stirring fan. The geometry of the vents cooperates with the axial and radial components of the stirring fan to promote conical vortex air flow, to facilitate rapid and controllable mass-flow interchange with ambient air. The resulting cooling performance in a small GC oven promotes more rapid requilibration between runs, control at temperatures closer to ambient, and the reduction of thermal overshoot; thus enhancing the performance and productivity of a field instrument.

15 Claims, 4 Drawing Sheets

GAS CHROMATOGRAPHY SYSTEM WITH THERMALLY AGILE OVEN

BACKGROUND OF THE INVENTION

The present invention relates to analytical systems and, more particularly, to gas chromatography systems. A major objective of the invention is to provide a compact, thermally agile, gas chromatography system.

Gas chromatography (GC) is a method of separating volatile organic and inorganic sample components. In GC, a sample is progressively heated through the boiling points of its components so that they can be differentially swept through a sorbent-coated column by a carrier gas. Components are separated according to the extent they preferentially bind to the sorbent material. To ensure maximum resolution, spatial temperature gradients in the column should be minimized. The required isothermal conditions are achieved by careful design of the heating system and oven geometry and by use of a fan to promote thorough mixing of the air that circulates past the column.

To ensure repeatability and comparability of results with standard retention-time tables, a GC oven must regulate temperature to match a selected demand ramp (or, more precisely, "demand function"). A demand ramp is a prescribed temperature-versus-time function that generally includes one or more periods of constant positive slope. In addition, a demand ramp can include one or more constant temperature periods to stabilize conditions at the beginning and/or end of a run, or to dwell temperature that favors separation of closely eluting components, thus, creating, so to speak, a chromatographic "sweet spot."

Typically, oven temperature is monitored during a ramp so that it can be compared with the temperature assigned at any given instant by the demand ramp. If the measured temperature is below the demand temperature, the power to the heater is increased. If the measured temperature is above the demand temperature, the power to the heater is decreased.

If the temperature remains high after power to the heater has been decreased to zero, the error cannot be corrected by further control of the heater. This problem typically arises when heat contributed by uncontrolled heat sources, even with the heater power off, exceeds that required by the demand ramp.

There are several such uncontrolled heat sources. Capillary inlets and outlets are continuously heated to avoid condensation; thus, these inlets and outlets function as uncontrolled heat sources that can raise the oven temperature even while the main heat source is off. In addition, heat dissipated by a stirring fan is an uncontrolled heat source. Even the heating element, to the extent that its thermal mass prevents instantaneous control of its output, can be considered to be in part a source of uncontrolled heat.

Furthermore, heat remaining in oven insulation from prior sample runs functions as an uncontrolled passive heat source. This last uncontrolled heat source can be addressed by allowing a longer cool down period between runs. Note that insulator heat is lower for a first run than for subsequent runs. This causes the first run to not be precisely comparable to subsequent runs. This phenomenon is known as the "first run effect". Often the first run is simply discarded at the expense of instrument productivity.

Long cooldown periods are undesirable because they lengthen the sample cycle time, further reducing instrument productivity. Most GC ovens employ ventilation in some form to increase the rate of heat removal during cool down. Furthermore, the availability of ventilation during a ramp means that heat remaining in the insulation does not have to be fully removed between runs. Thus, ventilation reduces cooldown time in two ways: 1) the availability of ventilation for ramp temperature control reduces the amount of cooling required between runs; and 2) the use of ventilation during cooldown decreases the time required to achieve a required amount of cooling.

A ventilation system used for ramp control must be carefully designed so that the ventilation does not introduce temperature gradients in the column. To minimize local temperature deviations at the column, the ventilation can be mixed with circulating air in a separate stirring chamber at the rear of the oven enclosure.

In one exemplary oven, intake and exhaust vents on the rear face of the oven enclosure can be used to cool the air in a stirring chamber to the rear of a main "column" chamber. Air from the stirring chamber is then circulated with air in the column chamber. The main chamber and stirring chamber are separated by a partition. The partition is spaced from the top and side faces of the oven enclosure to define an annular aperture through which stirred air flows to the main chamber. An aperture through the center of the partition provides a return path to the stirring chamber. A fan in the stirring chamber mixes ventilation flow with circulation flow and forces the mixed air out through the annular aperture.

Even with the use of ventilation during cooldown to increase the rate of cooling and the use of ventilation for near-ambient temperature control to reduce the amount of cooling required, instrument performance and productivity can be limited. A typical ramp from near-ambient temperature to a maximum of about 400° C. consumes about one-half hour, while another half hour can be required for cooldown for a full-hour cycle time. Near ambient temperature control is not generally available within 10° C. of ambient. Given the insatiable demand for GC performance and productivity, control at lower temperatures as well as faster ramp and cooldown times are sought.

To provide a fast run, a demand ramp can have a steep positive slope to a maximum temperature, at which the slope drops suddenly to zero (followed by a negative slope during cooldown). The fast ramp requires a heating element that is much hotter (e.g., 100° C. hotter) than the temperature at the column. When the heating element is turned off at the maximum demand column temperature (e.g., 400° C.), the heating element continues to glow for several seconds due to its thermal mass. The resulting excess heat causes the column temperature to surpass the demand maximum by several degrees. A similar overshoot can occur at an intermediate temperature; a user can select a ramp that has a sudden reduction of slope at an intermediate temperature selected to promote separation of otherwise difficult-to-separate sample components.

One problem with thermal overshoot is that the oven temperature temporarily deviates from the demand ramp; this makes it difficult to compare a chromatogram obtained using one manufacturer's GC system with those from other manufacturers and with standard retention-time tables. Another problem that is not widely recognized in the art can be an even greater concern. During overshoot, the oven temperature is not controlled and is therefore variable from run to run according to such factors as external temperature and first run effect. Thus, thermal overshoot impairs comparison of chromatograms even across successive runs from the same instrument.

One approach to minimizing thermal overshoot would be to "smooth" or "round" demand ramp corners (slope transition points). Since there are many ways of rounding a corner, this approach introduces another variable along which instruments can differ; this makes inter-instrument comparisons and comparisons with standardized retention-time tables problematic.

In addition to problems with instrument productivity and with reproducibility due to temperature control, it is well recognized that GC ovens are undesirably large. GC ovens typically constitute over half the volume of a GC system, which in turn consumes valuable laboratory bench space. What is needed is a compact, thermally agile GC system that provides for fast ramps and quick cooldowns, closer-to-ambient temperature control, and minimal thermal overshoot.

SUMMARY OF THE INVENTION

The present invention provides a thermally agile gas chromatography system comprising: 1) a sample manipulation assembly including a GC column, a sample source, and a detector; and 2) an oven including a chamber enclosure, a heat source within the oven, a ventilation system, and a temperature ramp controller. In accordance with the present invention, a ventilation fan is disposed between the ventilation intake and exhaust vent apertures so that its rotational axis extends through both apertures. The effective diameter of the intake aperture is preferably less than the effective diameter of the exhaust aperture. Preferably, the GC column is wound as a coil having an axis of cylindrical symmetry coincident to or parallel to the fan axis.

In one realization of the invention, each vent includes a poppet that can be moved to selectively open and close the including vent. The ramp controller can move the intake and exhaust puppets concurrently to implement at least part of a temperature ramp. Preferably, the poppets are rigidly coupled so that a single servo motor can be used to control ventilation through vents by moving the puppets along the fan axis. Provision is made for decoupling the puppets to provide access to the oven cavity through the exhaust vent.

A further aspect of the invention provides a support within the oven that holds and slightly radially compresses a helically wound capillary GC column. This arrangement provides a simple and secure method of holding the GC column in place over the wide temperature range imposed by the GC oven. The arrangement further disposes of unreliable attachment clips, or other structures, used to secure columns to internal supports.

The novel ventilation arrangement provides a low-resistance flow path directly through the helically wound column. The combination of a radially inward rear vent aperture and a relatively large radius front aperture accommodates the centrifugal effect of the stirring fan on the ventilation flow. Thus, the invention provides a near optimal direct conical flow path through the oven that facilitates the thousands of air interchanges required to remove the thermal energy stored in the oven insulation. The flow can be further enhanced by angling the fan blades forward.

The ventilation flow is also symmetrical about the fan axis. Where the column is in the form of a helix that is coaxial with the fan, a circumferentially uniform temperature is presented to the column. Thus, the ventilation does not induce thermal gradients in the column. Due to the inherent thermal symmetry, a separate stirring chamber is not required to mix ventilation flow with circulation flow. Thus, there is no partition to impede ventilation flow. By omitting the partition, the bulk and thermal mass of the oven are reduced, and the cooling efficiency increased.

The resulting efficient ventilation flow provides for mass transfer cooling several orders of magnitude greater than is provided by prior art GC ovens. Accordingly, cooldown time can be reduced by an order of magnitude. Cooperative movement of vent poppets along the fan axis provides precise control of the ventilation rate throughout a wide dynamic thermal range. The precisely controlled cooling can be used to compensate uncontrolled heat sources so as to tightly control ramp temperatures while only a few degrees Celsius above ambient.

In addition, efficient and precisely controlled ventilation can be used at intermediate and high temperatures to minimize overshoot even for ramps with sudden slope reductions. This affords a user a much wider selection of demand ramps, including ramps that provide for greater sample throughput as well as ramps that dwell on a selected chromatographic "sweet spot" without prolonging the rest of the ramp. By rapidly opening and closing the vents slightly at the time overshoot would occur, the overshoot can be snubbed (i.e., "cut off"). Thus, the present invention provides a "thermally agile" oven that allows a wider range of demand ramps to be tracked precisely.

The present invention provides excellent downward scalability. While some uncontrolled heat sources scale downward with oven dimensions, others do not. For example, insulation bulk decreases with downward scaling and therefore is of less concern as a heat source. However, heat sources such as capillary inlets and detectors do not scale proportionally to oven size; as an oven design is scaled downward, they constitute an increasingly significant source of uncontrolled heat. Thus, while ventilation capacity reduces with vent aperture diameters in proportion to oven size, the heat that must be removed by the ventilation does not scale to the same extent. The net effect is that the minimum controllable ramp temperature increases with decreasing oven size.

This principle applies to the present invention as well as to the prior art. However, some of the superior ventilation effectiveness of the present invention can be traded for compactness, resulting in an oven which is both smaller and better at near-ambient temperature control than prior art GC ovens. In fact, the present invention can provide a field-portable GC system that has higher performance than prior art laboratory GC systems.

In the case of the prior art, scaling a laboratory size oven to a size practical for field use would increase the minimum usable temperatures from about fifteen degrees Celsius above ambient to, for example, a not-very-useful sixty degrees Celsius above ambient. In the case of the present invention, a corresponding reduction in scale would raise the minimum temperatures from less than one degree Celsius above ambient to only a few degrees above ambient. Thus, the present invention provides for a high-performance, field-portable GC system.

The advantages of a high-performance, field-portable GC system are substantial, especially in applications such as contamination cleanup. Contamination cleanup can involve removal of large quantities of material, e.g., soil contaminated with industrial waste. The bulk and potentially hazardous character of the contaminated soil makes removal expensive and cumbersome. It is therefore important to determine onsite when all the contaminated material has been removed so that money and effort are not wasted on removing uncontaminated material. Such an onsite determination can be made with a field-portable GC system.

Furthermore, since sample components can degrade during transit to a laboratory, field-portable GC systems can provide more accurate analyses. More generally, the delay involved in transit, laboratory backlog, and delays in communication of lab results often takes two weeks which is often unacceptable. The delay is particularly harmful when the laboratory results indicate that further collection is required, especially where the further collection involves returning to a remote site. A high-performance, thermally agile, field-portable GC oven system addresses all these problems.

The present invention provides a compact, thermally agile GC oven. In addition, some thermal agility can be exchanged for field portability, while achieving GC performance superior to prior art laboratory GC systems. These and other features and advantages of the present invention are apparent from the description below with reference to the following drawings.

DESCRIPTION OF THE PREFERRED EMBODIMENTS

Figure 1:
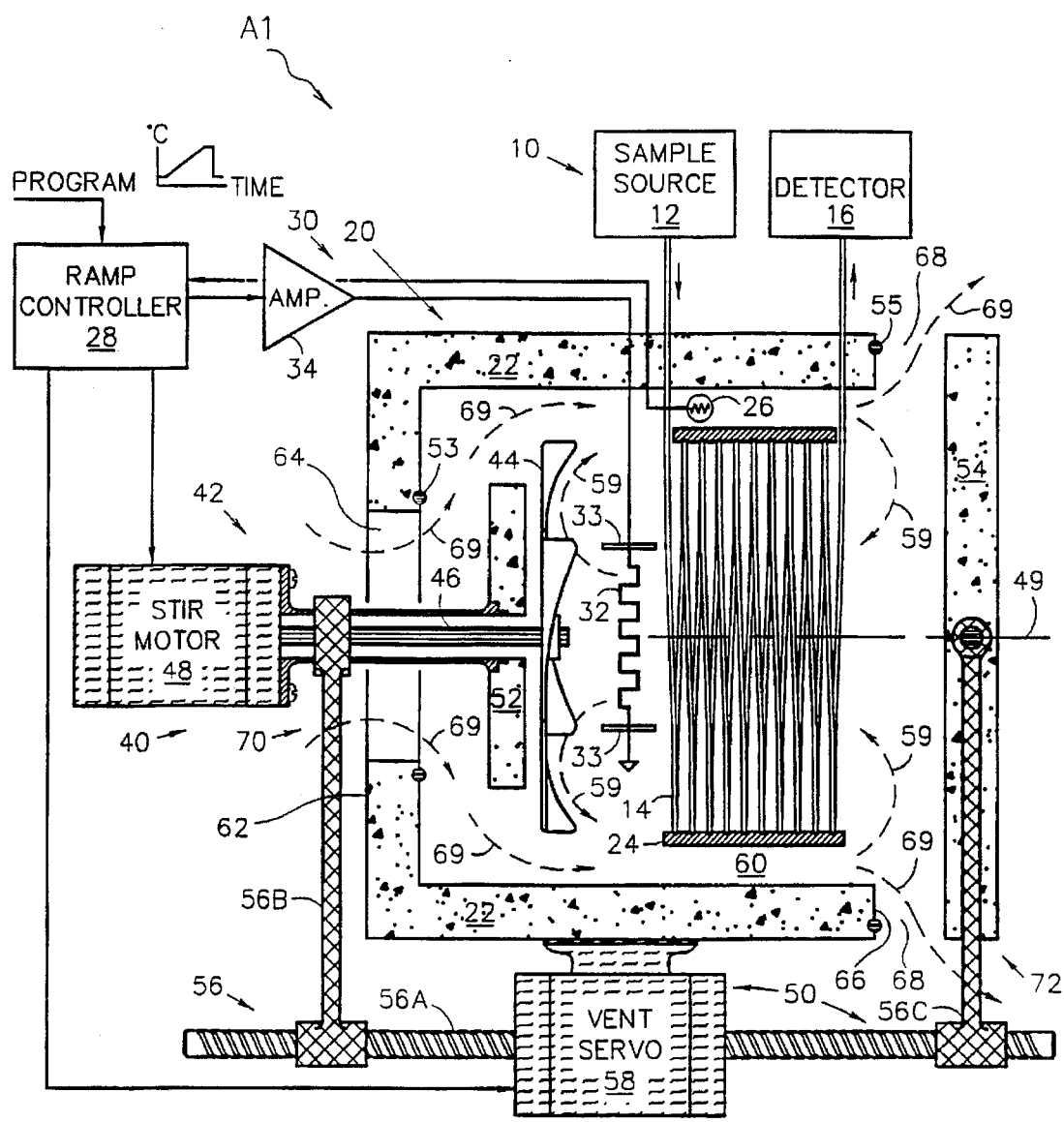
FIG. 1 is a schematic diagram of a gas chromatography system in accordance with the present invention.

In accordance with the present invention, a gas chromatography system A1 comprises a sample handler 10 and an oven 20. Sample handler 10 includes a sample source 12, a helically wound sorbent coated column 14, and a detector 16. Sample source 12 conventionally includes a sample injection port, a carrier gas source, and a flow controller. The sample injection port is hydraulically coupled to an inlet end of the column, while an effluent end of the column is hydraulically coupled to detector 16. Oven 20 includes an insulated chamber enclosure 22, a column support assembly 24, an oven temperature sensor 26, a ramp controller 28, a heating system 30, and a ventilation subsystem 40. Heating assembly 30 includes a resistive heater 32 and an amplifier 34. To either end of heater 32 are shields 33 to protect column 14 from direct radiant heat.

Ventilation system 40 includes a fan assembly 42 and a vent assembly 50. Fan assembly 42 includes a fan 44, a fan shaft 46, and a fan motor 48. Vent assembly 50 includes an intake poppet 52 with an associated ring seal 53, an exhaust poppet 54 with an associated ring seal 55, a carriage assembly 56, and a vent servo 58. In FIG. 1, vent poppets 52 and 54 are shown in their fully open ventilation positions.

Carriage assembly 56 is indicated schematically in FIG. 1 by a lead screw 56A, a rear linkage 56B to intake poppet 52, and a front linkage 56C to exhaust poppet 54; the preferred constitution for carriage assembly 56 is presented below with references to FIGS. 3 and 4. During a temperature ramp, poppets 52 and 54 are rigidly coupled in the sense that they, together with carriage assembly 56 that couples them, define a rigid body.

Fan 44 is located within oven cavity 60 between intake aperture 64 and exhaust aperture 68. Fan 44 rotates about a fan axis 49 that extends through the centers of vent apertures 64 and 68 as well as the center of the helix defined by column 14. When closed, ventilation system 40 effects circulation as indicated by arrows 59. The predominant flow with vents fully open is indicated by flow arrows 69. The generally direct conical flow path through chamber enclosure 22 provides high ventilation efficiency with thermal symmetry at column 14. In alternative embodiments, the fan axis extends through intake and exhaust apertures without being aligned with the aperture centers.

Chamber enclosure 22 defines an oven cavity 60 that contains column 14, column support assembly 24, sensor 26, resistive heater 32, fan 44 along with a portion of fan shaft 46, and intake poppet 52 (along with a portion of carriage assembly 56 during ventilation). Chamber enclosure 22 has an opening through its rear face 62 defining an intake aperture 64; chamber enclosure 22 is open at its front face 66, defining an exhaust aperture 68. Intake aperture 64 and intake poppet 52 constitute a controllable intake vent 70; exhaust aperture 68 and exhaust poppet 54 constitute a controllable exhaust vent 72.

A demand ramp is selected by programming ramp controller 28. Typically, the ramp includes constant temperature periods and periods of constant positive slope. In system A1, the maximum slope is about 2° C. per second (about five times the rate of prior art GC ovens).

When the measured temperature deviates from demand temperature, ramp controller 28 implements an error response algorithm to control power to heater 32 and the opening and closing of ventilation subsystem 40. Generally, errors are compensated primarily by adjusting the power to heater 32 while vents 70 and 72 are closed and by adjusting the vents while the vents are open. To avoid singularities in the error response, the heating and ventilation error responses are cross-faded. For examples, the heater can start heating before the vents are fully closed, and the vents can begin to open before the heater is turned completely off.

Ramp controller 28 is coupled to the output of oven temperature sensor 26 for monitoring the temperature within oven cavity 60 to provide a measured temperature readout. The measured temperature is used first to determine when to begin a ramp. Between runs it takes time to cool down to the initial temperature for the next ramp. Once a desired initial minimum temperature is reached, a typical demand ramp holds the minimum temperature for a few seconds to allow the thermal conditions in oven 20 to stabilize. For GC system A1, the stabilization temperature can be as low as a few degrees Celsius above ambient.

Ventilation subsystem 40 is partially open most of the time during stabilization. To adjust ventilation, ramp controller 28 actuates vent servo 58, which drives carriage assembly 56. Intake poppet 52 and exhaust poppet 54 are rigidly coupled to drive carriage assembly 56 so that they open and close in unison. During a stabilization interval and before ventilation system 40 is completely closed, ramp controller 28 activates current source 34, which is electrically coupled to resistive heater 32. Thus, heating begins as ventilation subsides, as dictated by the implemented cross fade.

The positive slope portion of a ramp typically begins with ventilation subsystem 40 closed; heater 32 is controlled to maintain a differential relative to the demand temperature. The differential increases with temperature to compensate for greater thermal losses. Once a maximum demand temperature is achieved, ventilation subsystem 40 can be opened briefly to control overshoot as the demand temperature levels off. Between runs, ramp controller 28, upon sensing an enormous disparity between the demand and the measured temperature, fully opens ventilation subsystem 40, thereby minimizing cooldown time.

Ramp controller 28 constantly compares measured and demand temperatures and implements proportional-integrated-differential (PID) error correction. If the measured temperature falls below the demand temperature, the current is further increased. If the measured temperature rises slightly above the demand temperature, the current is reduced or turned off. If reducing heat input does not fully compensate for overheating, ventilation subsystem 40 is opened.

Figure 2:
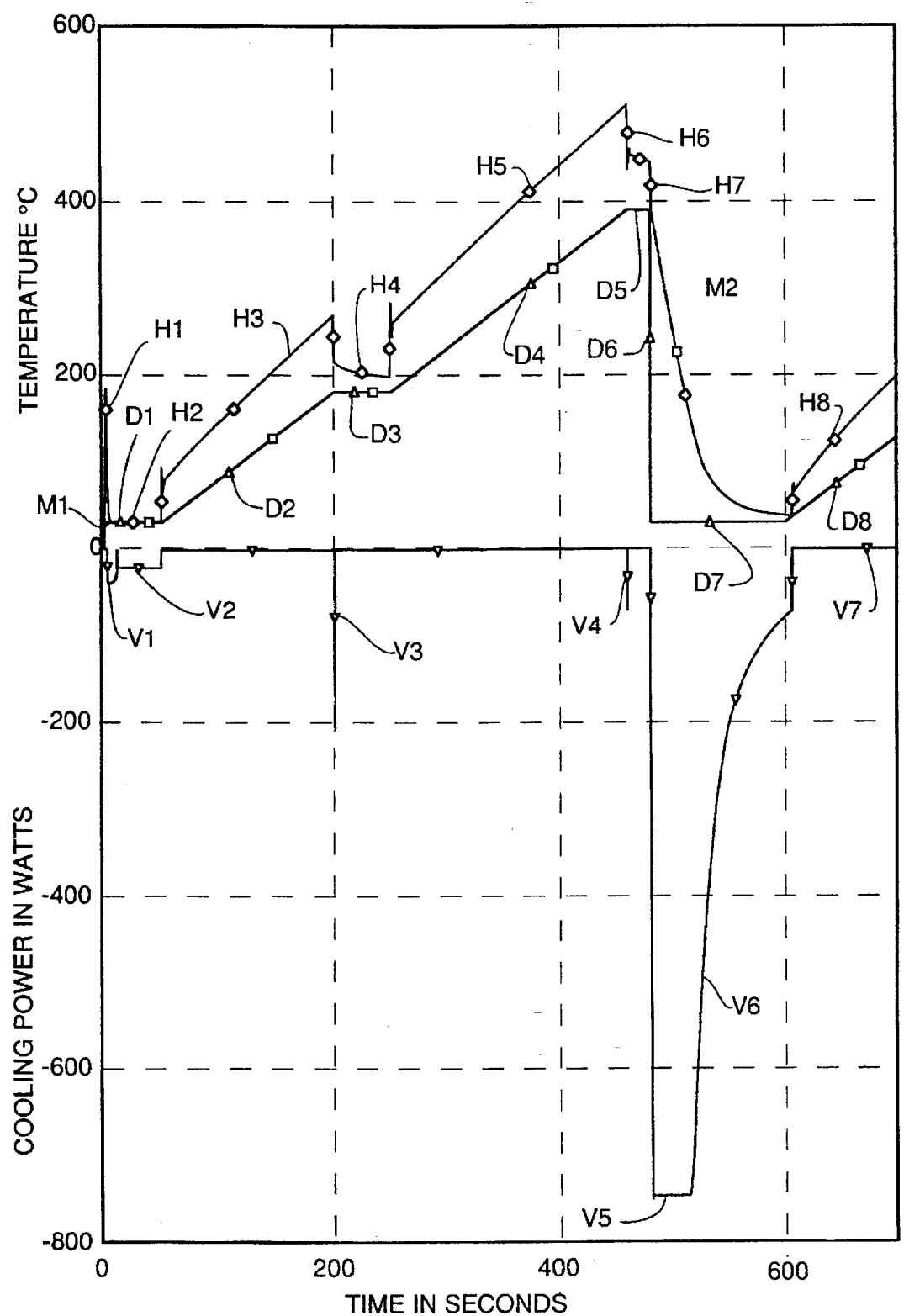
FIG. 2 is a graph of power removal and temperature over time characterizing the operation of the gas chromatography system of FIG. 1.

The functioning of GC system A1 is indicated in the graph of FIG. 2, which shows four time-varying variables: 1) the temperature demand ramp is indicated by a line marked with squares; 2) the measured temperature is indicated by a line (which, for the most part coincides with the demand temperature) marked with circles; 3) the heater temperature is indicated by a line marked with downward pointing triangles; and 4) the amount of heat (in watts) being removed by ventilation is indicated by a line marked with upward pointing triangles. To accentuate certain features, crossfading is only minimally implemented in the sample runs depicted in FIG. 2.

The demand ramp begins with an initial constant temperature period D1 at 30° C., followed by a period D2 of constant positive slope, followed by a period D3 of constant temperature (e.g., at a chromatographic sweet spot), followed by another period D4 of constant positive slope, followed by a period D5 at a constant maximum temperature near 400° C. The next period D6 is a drop to the minimum temperature in preparation for a second sample run. A period D7 is a constant minimum temperature to stabilize conditions for the second run. The final illustrated second-run period D8 has a constant positive slope.

As would be desired, the measured temperature tracks the demand temperature precisely during sample runs. Before the first run, the measured temperature is at ambient, 25° C. The minimum demand temperature of 30° C. is achieved within the few seconds of a period D2. At this point, the first sample run can begin. During the first and subsequent sample runs, measured temperature matches demand temperature as required. Of course, the measured temperature cannot match the precipitous drop of the demand ramp cooldown period D6. During cooldown at period D2, the measured temperature approaches the constant minimum demand temperature asymptotically, stabilizing near the end of period D7.

The heater is turned on briefly and fully at H1 at the onset of the stabilization portion of the demand ramp. It should be noted that the maximum temperature that the heater can attain is limited by the surrounding temperature. The peak at H1 represents the maximum temperature the heater can achieve at the initial, first-run, 25° C. (ambient) temperature of the oven. Once 30° C. is achieved, the heater is turned off, as indicated at H2. The heater is turned on again at H3 during positive sloping period D2 of the demand ramp. The temperature of the heater is increased to maintain a gradually increasing differential temperature relative to the measured temperature to compensate for greater heat loss at higher oven temperatures.

The heater temperature is suddenly reduced (by temporarily turning off the power to the heater) at the onset of sweet spot period H4, and then gradually reduced to maintain a constant measured temperature. Heater period H5 begins with a sudden increase in heater temperature and then is positively sloping to achieve a gradually increasing temperature differential relative to positively sloping period D4 of the demand ramp. The heater power is briefly turned off at the onset of heater period H6 to implement constant maximum demand temperature period D5. The heater is off at H7 so that the temperature of the heater element quickly drops to the oven temperature. During cooldown period D2, during which the heater temperature tracks the measured oven temperature.

The heater is turned on again to initiate heater period H8. The heater temperature is increased to maintain a gradually increasing differential relative to demand period D8. This differential is smaller in period H8 than for period H3 because of the first run effect. In other words, stored heat deep inside the chamber insulation contributes more heat during second run period H8 than during first run period H3.

Ventilation subsystem 40 is opened briefly at period V1 primarily to compensate for excess heat from heater 32 after power to heater 32 is removed. Ventilation subsystem 40 is opened slightly during period V2 primarily to compensate for constant uncontrolled heat sources while oven temperature stabilizes. A brief vent opening at V3 is used to compensate for thermal overshoot as sweet spot period D3 is reached. Similarly, a brief vent opening at V4 compensates for thermal overshoot as maximum demand period D5 is reached. Ventilation subsystem 40 is fully open at V5 to maximize heat transfer during cooldown period M2. Note that the reduction in cooling at V6 is not due to the closing of vents, but to the reduced differential between internal oven temperature and the ambient temperature. Ventilation subsystem 40 is closed at V7 to initiate second sample period D8.

Figure 3:
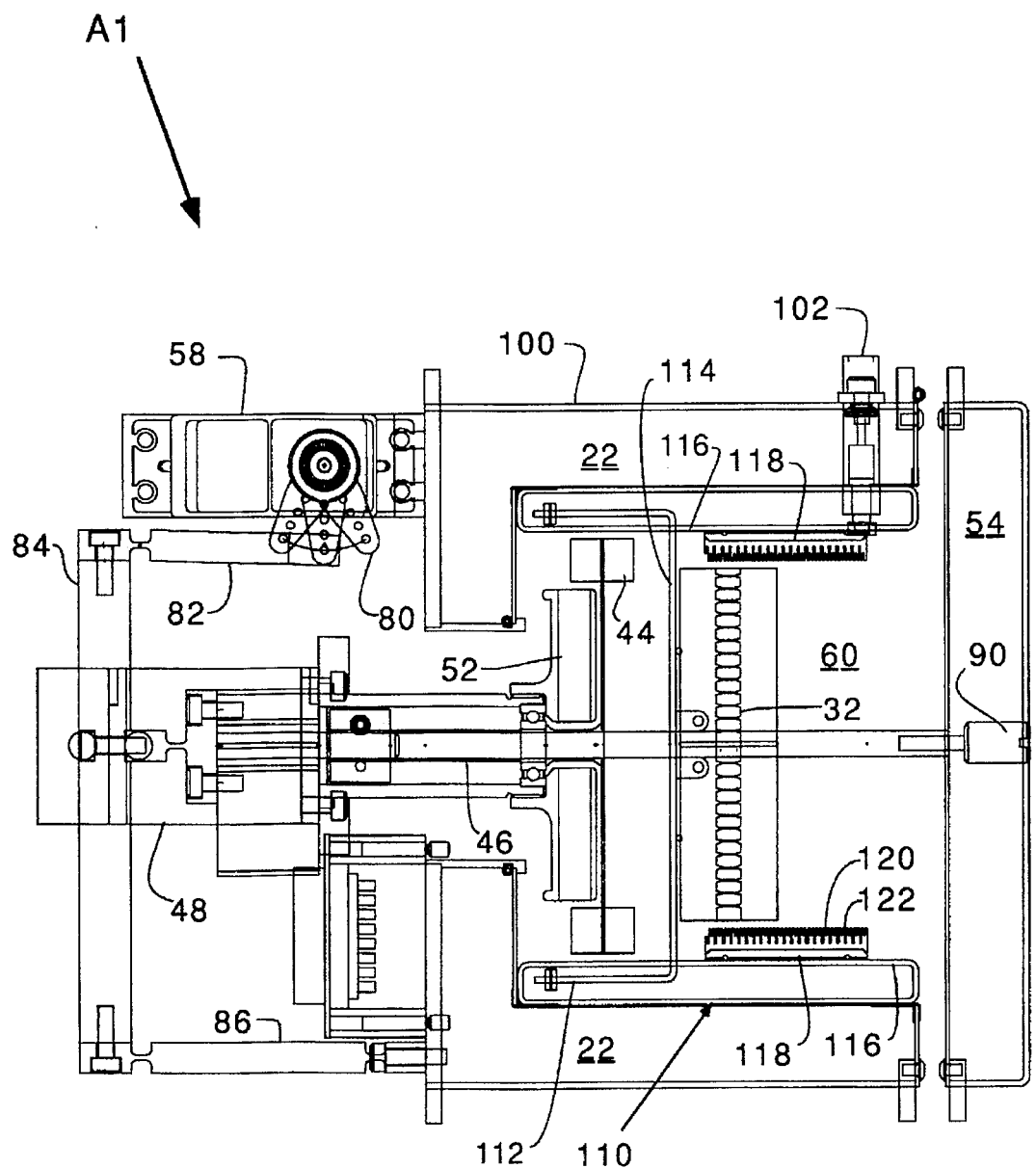
FIG. 3 is a view through the right side of a gas chromatography oven of the GC system of FIG. 1.

As most clearly shown in FIG. 3, vent servo 58 has a pivoting armature 80 that couples to a linkage 82 that in turn couples to a carriage 84. Fan motor 48 and intake poppet 52 are rigidly coupled to carriage 84 so that these elements move along fan axis 49 when vent servo 58 is actuated. Fan shaft 46 and fan 44 also move along axis 49 by virtue of their coupling to fan motor 48. A guide rod 86 helps stabilize the axial motion of carriage 84.

Figure 4:
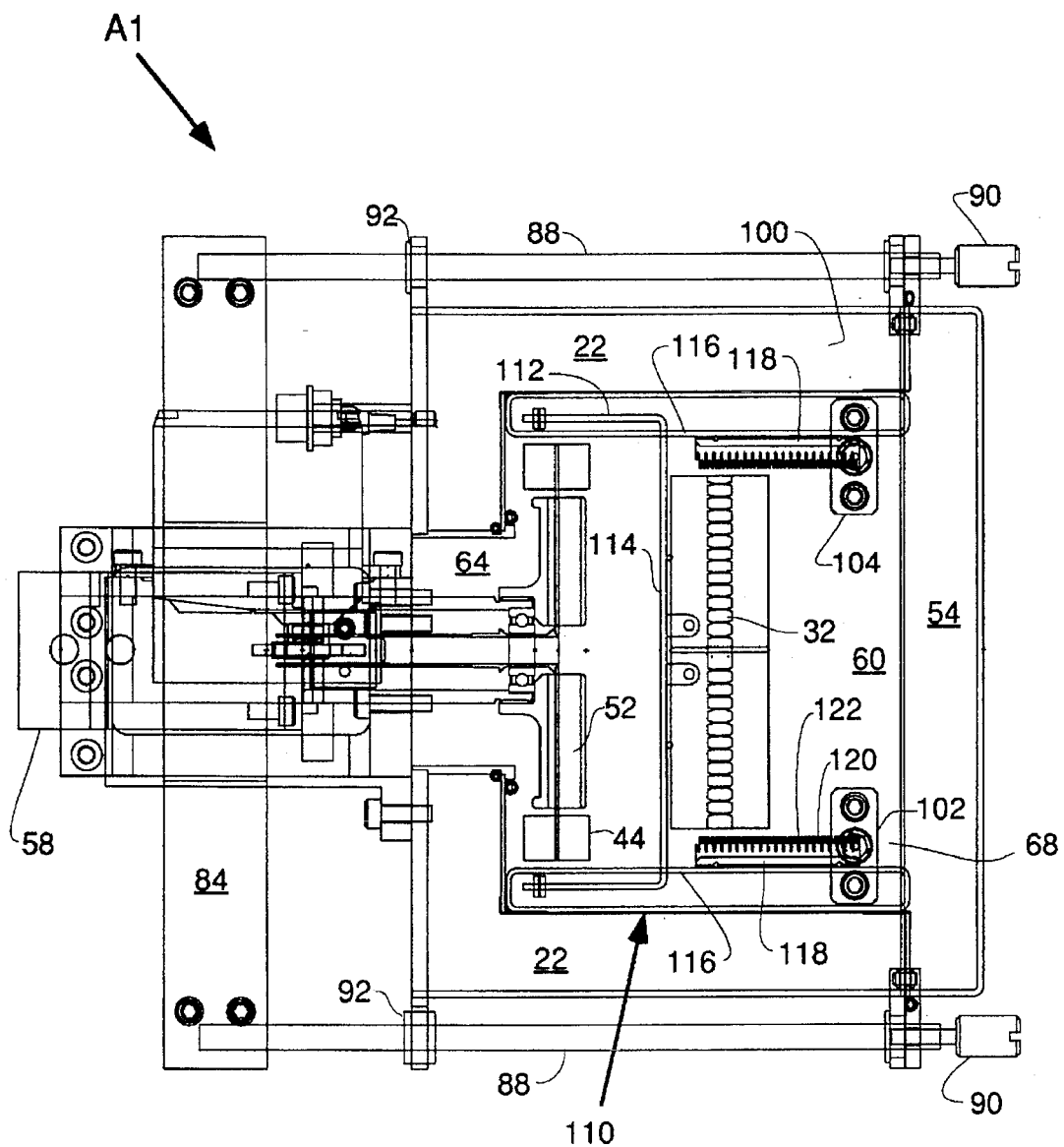
FIG. 4 is a view through the top of the GC oven of FIG. 2.

As most clearly shown in FIG. 4, exhaust poppet 54 is attached to a pair of rods 88 by fasteners 90. Access to oven cavity 60 can be obtained by removing fasteners 90 and exhaust poppet 54. Rods 88 are rigidly coupled to carriage 84. Rods 88 slide relative to chamber enclosure 22 through journals 92 attached to chamber enclosure 22. Poppets 52 and 54 open and close intake and exhaust apertures 64 and 68 in unison when vent servo 58 is actuated. Note that carriage assembly 56 of FIG. 1 comprises carriage linkage 82 shown in FIG. 3, carriage 84 shown in FIGS. 2 and 3, guide rod 86 shown in FIG. 3, and exhaust poppet rods 88 shown in FIG. 4.

On a top face 100, shown in FIG. 3, of chamber enclosure 22, is a detector mount 102 for detector 16 (shown in FIG. 1). Also on top face 100, is an injector mount 104 for the injection port of sample source 12, shown in FIG. 4. Shown in both FIGS. 3 and 4 is a capillary support assembly 110 that includes resistive heater 32. Assembly 110 can be removed from oven cavity 60 when exhaust poppet 54 is removed. When inserted into cavity 60, a cylindrical skirt 112 frictionally engages chamber enclosure 22. A base 114 of resistive heater 32 is bolted to skirt 112. Welded to skirt 112 are four spring supports 116, each of which supports a respective capillary support post 118. (Two supports and two posts are shown in FIG. 3 and the other two supports and the other two posts are shown in FIG. 4.)

Each capillary support post 118 includes alternating shallow grooves 120 and deep grooves 122, referenced in FIG. 3. Grooves 120 and 122 are dimensioned to engage the turns of capillary column 14. Deep grooves 122 hold the turns from injection source 12 that wind from the front to the back of oven cavity 60. Shallow grooves 120 hold the turns as the capillary helix returns from back to front to detector 16. Spring supports 116 provide low-thermal-mass support for capillary column 14 and apply a slight compression to the helical form of column 14.

Resistive heater 32 is a low mass heater, allowing higher servo gain increased accuracy and reduced overshoot. It is fabricated from a nickel-chrome alloy, such as nichrome, which is flattened to maximize the convective heat transfer from it while at the same time minimizing its thermal mass.

Fan motor 48 is a brushless motor so as to further optimize dynamics by reducing the time constant of the heater; it combines the speed of a brush motor with the reliability and explosion proof characteristics of induction motors. Fan 44 is mounted on thin, low-conductivity titanium alloy hollow shaft 46 so as to minimize conductive heat loss into fan motor 48.

By using a single structure for both the exhaust poppet and the access door, shunt conductive paths are minimized and simplified. This reduces static thermal loss from the oven to the ambient. This in turn, enhances the thermal efficiency of the oven. In practice, oven 20 can implement a full-range 30° C. to 400° C. ramp and re-equilibrate with a cycle time of only eight minutes (about six minutes for the sample run plus about two minutes for cooldown).

Unlike ovens used for other applications, e.g., cooking, the thermal mass of oven 20 is minimized to enhance dynamic performance. Toward this end, the insulator is 0.8 pounds per cubic foot (pcf) micropore ceramic fiber and the chamber wall liner is 0.010" stainless steel. Such insulation has low thermal conductivity and yet low thermal capacity. Alternatively, other low-density insulators, such as Aerogel (available from Aerojet Corporation, Sacramento, Calif.) can be used. In a dynamic oven, the mass of the inner layers of the insulation must be carried up to near oven temperature. Further, most of the heat absorbed by the insulation must be pumped out during the cooling cycle. The low thermal conductivity of the ceramic fiber insures effective insulation, while the low thermal capacity facilitates rapid cooldown. Where it is necessary to couple interior and exterior surfaces, e.g., at vent openings, mica board is used to separate stainless steel liners to minimize conduction from interior to exterior.

The external dimensions of oven 20 are about 150 millimeters (mm)×150 mm×150 mm, providing internal dimensions of about 100 mm (wide)×100 mm (high)×70 (deep-between apertures 64 and 68). The total mass is about 1.5 kilograms. The linear dimensions are less than half those of comparable prior art GC systems. The volume and mass are about an order of magnitude less than comparable prior art GC systems. Furthermore, while prior art GC systems can require kilowatts of power or more, the total power consumption of system A1 need not exceed 350 watts. Such power can be readily provided by an inverter from a vehicle or by a field-portable generator. Interfacing for system A1 can be provided by a laptop computer, completing the miniaturized field-portable package.

While in the preferred embodiment, the fan axis extends through the centers of the intake and exhaust apertures, in alternative embodiments, the axis extends through these apertures off center. In an alternative embodiment, an exhaust poppet is hinged and lockable. When locked, it is rigidly coupled to an intake poppet; when unlocked, it swings open to provide access to the oven cavity. These and other variations upon and modifications to the embodiments described above are provided for by the present invention, the scope of which is defined by the following claims.

What is claimed is:

1. A method for controlling the temperature of a gas chromatography column in an oven having an intake vent and an exhaust vent, comprising:

generating heat in a heater in the oven to heat the oven and the column;

controlling the temperature the column, when the exhaust vent and the intake vent are closed, by blowing with a fan axially aligned with the intake vent and the exhaust vent to cause air to pass over the column and the heater; and cooling the column by opening the intake vent on an intake side of the oven to admit intake air into the oven and opening the exhaust vent on an exhaust side of the oven opposite to the intake side to discharge exhaust air and by blowing air with the fan, wherein the intake vent has an intake aperture and a movable intake poppet and the exhaust vent has an exhaust aperture and a movable exhaust poppet, and wherein opening the intake vent includes moving the intake poppet initially axially along an axis extending between said apertures to allow the intake air to enter said intake aperture, and opening the exhaust vent includes moving the exhaust poppet initially axially along said axis to allow air to exit the exhaust aperture.

2. A method as recited in claim 1 wherein in the step of cooling, the intake poppet and the exhaust poppet are moved along axial, straight, and parallel paths to open said vents.

3. A method as recited in claim 1 wherein the intake poppet is axially located relative to the intake aperture, and wherein the exhaust poppet is axially located relative to the exhaust aperture, and in the step of cooling, further comprising driving intake air into the oven cavity around the perimeter of the intake poppet, and venting exhaust air around the perimeter of the exhaust poppet.

4. A method as recited in claim 1 wherein in the step of cooling, further comprising driving intake air around the perimeter of the intake poppet and venting exhaust air around the perimeter of the exhaust poppet, wherein the perimeter of the exhaust poppet is larger than that of the intake poppet, such that the air flow is about conical from the intake vent to the exhaust vent and symmetrical about said axis.

5. A gas chromatography system comprising:

a gas chromatography column;

a sample source for introducing sample components into said column, said sample source being in fluid communication said column;

a detector for detecting sample components exiting said column, said detector being optically coupled with said column;

a chamber enclosure defining an oven cavity enclosing said column;

an adjustable heater located within said oven cavity;

a ventilation subsystem including an intake vent having an intake aperture and a movable intake poppet on an intake side of the chamber enclosure, said intake poppet having an open position causing the intake vent to be in an open condition, said intake poppet also having a closed position causing said intake vent to be in a closed condition, said input vent while in its open condition admitting air into said cavity, said input vent while in its closed condition preventing air from entering said cavity through said intake aperture, and an exhaust vent having an exhaust aperture and a movable exhaust poppet on an exhaust side of the chamber enclosure opposite the intake side, said exhaust poppet having an open position causing the exhaust vent to be in on open condition said exhaust poppet also having a closed position causing said exhaust vent to be in a closed condition, said exhaust vent while in its open condition allowing air to exit said oven cavity, said exhaust vent while in its closed condition preventing air from exiting said cavity through said exhaust aperture;

fan means for stirring air within said oven cavity while said intake vent and said exhaust vent are in their respective closed conditions and further for forcing air into said cavity through said intake aperture and forcing air out said exhaust aperture while said input vent and said output vent are in their respective open conditions, said fan means including a rotating element located between said intake vent and said exhaust vent, said rotational element rotating about an axis that extends through said intake aperture and said exhaust aperture; and temperature control means for implementing a temperature ramp of said column, said control means being coupled to said heater for controlling it, said control means being coupled to said ventilation system for opening and closing said intake vent and said exhaust vent.

6. A system as recited in claim 5 wherein said ventilation subsystem further includes vent drive means for controlling said intake poppet and said exhaust poppet so that:

they transition from their respective open positions to their respective closed positions concurrently; and they transition from their respective closed positions to their respective open positions concurrently;

said vent drive means being coupled to said temperature control means for control thereby.

7. A system as recited in claim 6 wherein said intake poppet and said exhaust poppet are rigidly coupled to each other.

8. A system as recited in claim 5 further comprising a column support physically coupled to said chamber enclosure, said column being helically wound and radially compressed within said support so that it pushes radially outward against said support.

9. A system as recited in claim 5 wherein the fan means and the column are arranged such that the column and the fan means are positioned on said axis such that during cooling, air is driven to travel from the intake vent passing over the heater and the column to the exhaust side of the oven, without substantial impedance by other structures.

10. A system as recited in claim 5 wherein the intake vent, exhaust vent and the fan means are arranged such that in a region along said axis between the column and the fan means air is driven to travel in the same direction when the exhaust vent is open and when it is closed.

11. A system as recited in claim 5 wherein the heater, the intake vent, the exhaust vent, and the fan means are arranged such that said axis passes through the heater as a whole.

12. A system as recited in claim 5 wherein the heater, column, the heater, the intake vent, the exhaust vent, and the fan means are arranged such that said axis passes through the heater as a whole and through the column as a whole and such that no other structure interposes to substantially impede air flow between the fan means, the heater, and the column.

13. A system as recited in claim 5 wherein in the intake vent the intake poppet is axially located relative to the intake aperture such that in the open condition intake air enters the oven cavity around the perimeter of the intake poppet, and wherein in the exhaust vent the exhaust poppet is axially located relative to the exhaust aperture such that in the open condition exhaust air exits the oven cavity around the perimeter of the exhaust poppet.

14. A system as recited in claim 5 wherein in the intake vent the intake poppet is axially located relative to the intake aperture such that in the open condition intake air enters the oven cavity around the perimeter of the intake poppet, and wherein in the exhaust vent the exhaust poppet is axially located relative to the exhaust aperture such that in the open condition exhaust air exits the oven cavity around the perimeter of the exhaust poppet, wherein the perimeter of the exhaust poppet is larger than that of the intake poppet, such that the air flow is about conical from the intake vent to the exhaust vent and symmetrical about said axis.

15. A gas chromatography system comprising:

a chamber enclosure defining an oven cavity;

a ventilation subsystem including an intake vent on an intake side of the chamber enclosure, said intake vent having an intake aperture and a movable intake poppet to open and close said intake aperture for open and closed conditions, said input vent while in its open condition admitting air into said cavity around the perimeter of the intake poppet, said input vent while in its closed condition preventing air from entering said cavity through said intake aperture, and an exhaust vent on an exhaust side of the chamber enclosure opposite the intake side, said exhaust vent having an exhaust aperture larger than the intake aperture and a movable exhaust poppet to open and close said exhaust aperture for open and closed conditions, said exhaust vent while in its open condition allowing air to exit said oven cavity around the perimeter of the exhaust poppet, said exhaust vent while in its closed condition preventing air from exiting said cavity though said exhaust aperture;

fan for stirring air within said oven cavity while said intake vent and said exhaust vent are in their respective closed conditions and further for forcing air into said cavity through said intake aperture and forcing air out of said cavity through said exhaust aperture while said input vent and said output vent are in their respective open conditions, said fan including a rotational shaft located between said intake vent and said exhaust vent, said rotational shaft being rotatable about an axis that extends through said intake aperture and said exhaust aperture;

an adjustable heater located within said oven cavity;

a gas chromatography column located within said oven cavity;

a sample source for introducing sample components into said column, said sample source being in fluid communication said column;

a detector for detecting sample components exiting said column, said detector being optically coupled with said column; and temperature control means for implementing a temperature ramp of said column, said control means being coupled to said heater for controlling it, said control means being coupled to said ventilation system for opening and closing said intake vent and said exhaust vent;

wherein the intake vent, fan, heater, column, and exhaust vent are arranged such that during cooling, air is driven to travel from the intake vent to pass over the heater and the column to the exhaust side of the oven about symmetrical around said axis in a conical fashion.

* * * * *